United States Patent [19]

Hartmann et al.

[11] Patent Number: 4,866,185

[45] Date of Patent: Sep. 12, 1989

[54] DIFUNCTIONAL POLYFLUOROAROMATIC DERIVATIVES AND A PROCESS OF PREPARING THE SAME

[75] Inventors: Ludwig A. Hartmann, Wilmington, Del.; John F. Stephen, West Chester, Pa.

[73] Assignee: ICI Americas Inc., Wilmington, Del.

[21] Appl. No.: 223,464

[22] Filed: Sep. 6, 1988

Related U.S. Application Data

[62] Division of Ser. No. 853,448, Apr. 18, 1986, Pat. No. 4,783,547.

[51] Int. Cl.$^4$ .................................. C07D 207/452
[52] U.S. Cl. ..................... 548/521; 548/522
[58] Field of Search ......................... 548/521

[56] References Cited

U.S. PATENT DOCUMENTS

| | | | |
|---|---|---|---|
| 3,694,495 | 9/1972 | Norris | 260/515 |
| 4,107,174 | 8/1978 | Baumann | 548/521 |
| 4,385,070 | 5/1983 | Bentley et al. | 424/305 |
| 4,486,355 | 12/1984 | Bentley et al. | 260/465 |
| 4,492,617 | 1/1985 | Davies | 204/73 |
| 4,517,129 | 5/1985 | Milner | 260/465 |
| 4,550,206 | 10/1985 | Richardson | 564/289 |
| 4,551,546 | 11/1985 | Punja | 560/124 |
| 4,567,199 | 1/1986 | Crowley | 514/531 |
| 4,654,407 | 3/1987 | Domeier | 548/521 |

FOREIGN PATENT DOCUMENTS

| | | |
|---|---|---|
| 1381223 | 11/1964 | France . |
| 3041456 | 2/1988 | Japan . |
| 1147067 | 4/1969 | United Kingdom . |
| 2123823A | 2/1984 | United Kingdom . |
| 2123824A | 2/1984 | United Kingdom . |
| 2135306A | 8/1984 | United Kingdom . |

OTHER PUBLICATIONS

Wagner, Peter J., et al., "Deactivation of Triplet Phenyl Alkyl Ketones by Conjugatively Electron-Withdrawing Substituents", J. Am. Chem. Soc., 1981 103, pp. 7329–7335.

Fuson, Reynold C., et al., "The Reaction of Grignard Reagents with the Cyanobenzoyldurenes", Journal of Organic Chemistry, V. 16, 1951, pp. 648–654.

Respess, W. L., et al., "Anomalous Reactions of Organomagnesium Reagents with Perfluoroaromatic Compounds", Journal of Organometallic Chemistry, 22 (1970) pp. 251–263.

Booth, B. L., et al., "Reactions of Metal Carbonyl Anions with Pentafluoropyridine and Pentafluorobenzonitrile", J. Organometal. Chem., 6 (1966) pp. 570–571.

Birchall, J. M., et al., "Polyfluoroarenes, Part XVII, some Reactions of Pentafluorobenzonitrile", Journal of the Chemical Society, (C), 1971, pp. 1343–1348.

Chem. Abstracts, vol. 78, 1973, Abstract No. 159147k.
Chem. Abstracts, voll 95, 1981, Abstract No. 80332j.
Chem. Abstracts, vol. 84, 1975, Abstract No. 16902r.

Primary Examiner—Mukund J. Shah
Assistant Examiner—Frederick F. Tsung

[57] ABSTRACT

The difunctional polyfluoroaromatic compounds represented by the formula $$X-\underset{F\ \ F}{\overset{F\ \ F}{C_6}}-CH_2-\left(\underset{F\ \ F}{\overset{F\ \ F}{C_6}}\right)_n-Y$$

wherein X and Y are identical and are selected from the class consisting of —COOR$^1$, —CH$_2$NH$_2$, —CH$_2$NCO and $$-CH_2-N\underset{C-C}{\overset{C-C}{\underset{\underset{O}{\|}}{\overset{\overset{O}{\|}}{\diagup}}}}\underset{R^3}{\overset{R^2}{\diagdown}},$$

wherein R$^1$ is —H, alkyl and R$^2$ and R$^3$ independently are either —H, X or alkyl and n is either 0 or 1 are disclosed. These compounds are derived from those wherein X and Y are —CN which are produced in a solvent specific reaction. The process comprises reacting pentafluorobenzonitrile with a Grignard reagent of the formula CH$_3$MgHal, wherein Hal is —Cl or —Br, in the presence of either tetrahydrofuran, 1,3-dioxolane, dimethoxyethane or diglyme. When the solvent employed is tetrahydrofuran, the cyano compound wherein n is 1 is obtained. When the solvent is 1,3-dioxolane, the cyano compound wherein n is 0 is obtained.

2 Claims, No Drawings

DIFUNCTIONAL POLYFLUOROAROMATIC DERIVATIVES AND A PROCESS OF PREPARING THE SAME

This is a divisional of co-pending application Ser. No. 853,448 filed on 4/18/86, now U.S. Pat. No. 4,783,547.

BACKGROUND OF THE INVENTION

The prior art has long recognized the versatility of perfluoroaromatic monomers in the production of polymers having high thermal stability. U.S. Pat. Nos. 3,694,495; 3,629,340 and 3,394,190 are exemplary of the use of such compounds as polymeric intermediates.

Further, such compounds have been employed as intermediates in the production of pyrethroid insecticides. For example, U.S. Pat. Nos. 4,385,070 and 4,486,355 disclose compounds of the formula

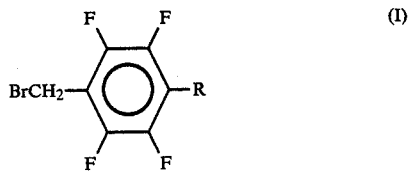

(I)

wherein R is nitro, cyano, lower alkoxycarbonyl, lower alkylcarbonyl, or di- or trifluoromethyl which are used as intermediates in the production of benzyl esters having insecticidal and acaricidal activity. The compound wherein R is —CN may be prepared by carboxylation of the corresponding methyltetrafluorobenzene and subsequent derivativization of the carboxylic acid group, as set forth below:

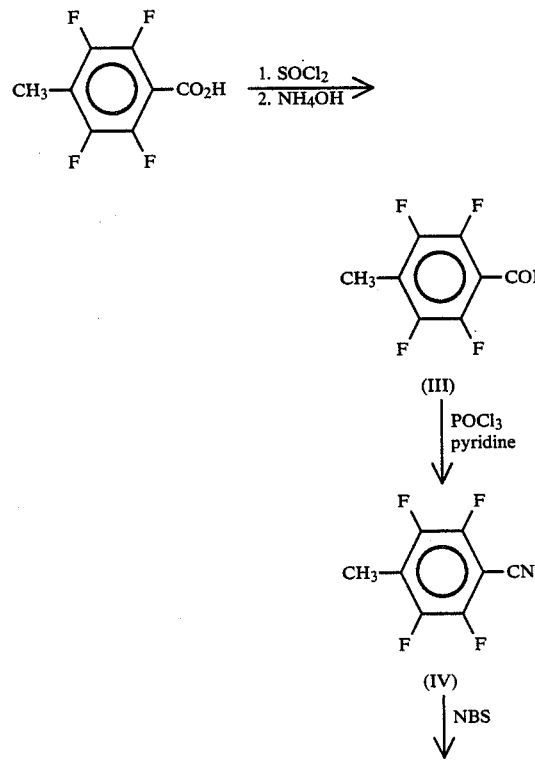

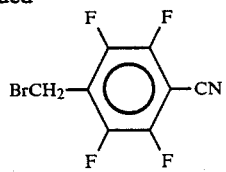

(V)

Since this reaction sequence and similar reaction sequences for producing such difunctional compounds are not particularly cost effective, alternative methods for the production of the difunctional intermediates are continuously being advanced.

A simplified method of producing para-substituted difunctional derivatives of pentafluorobenzonitrile would be by a Grignard synthesis.

However, the prior art teaches that the reaction of a Grignard reagent and a pentafluoroaromatic compound substituted with such electron withdrawing groups as —CN, —COR and —COOR, wherein R is an alkyl group, will not produce the desired para substituted compounds.

For example, Birchall et al in an early study illustrated that the reaction of pentafluorobenzonitrile (PFBN), represented by the formula

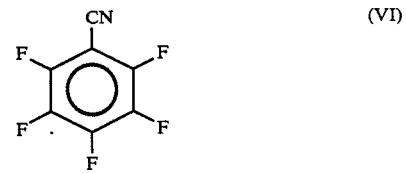

(VI)

with phenylmagnesium bromide in ether rendered pentafluorobenzophenone via the intermediate imine hydrochloride, $C_6F_5CPh:N^+H_2Cl$. (J. Chem. Soc. (C), 1971, 7, 1343).

Further, studies by T. N. Gerasimova show that when the starting reactants contain a —COOR group versus a —CN, the ortho substituted product is obtained, as represented by the following reaction mechanisms:

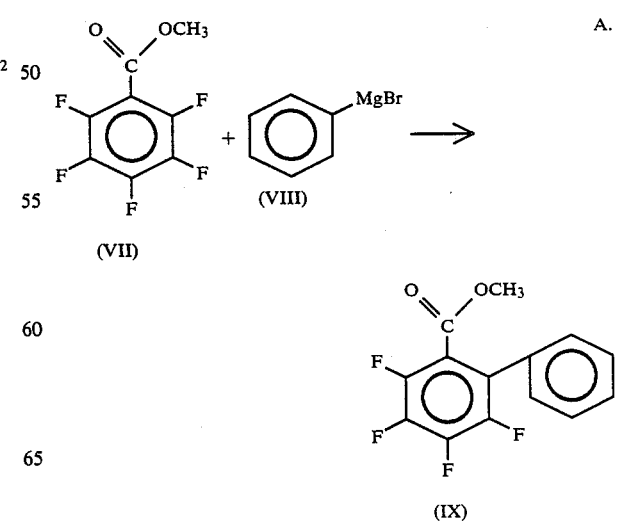

-continued

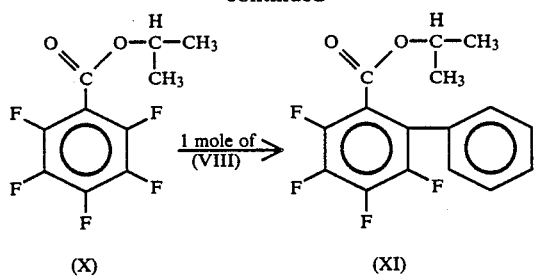

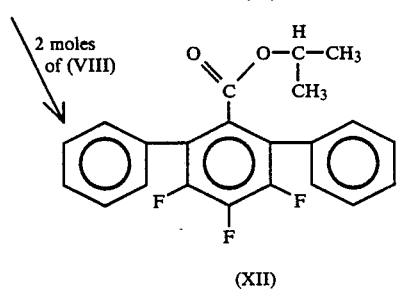

Zh. Org. Khim, 1973, 9(3), 639.

B.

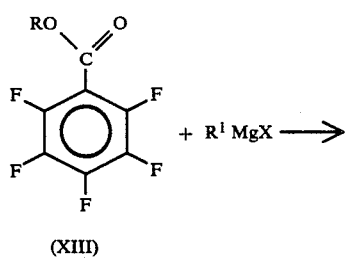

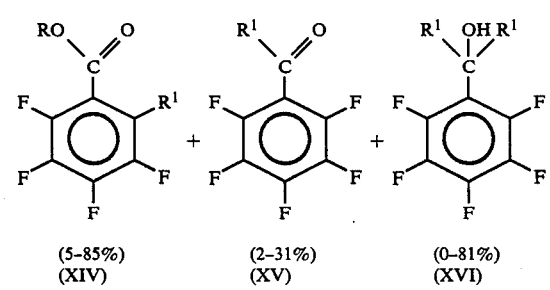

where R =—CH₃ or —CH(CH₃)₂; and R¹ =C₁—C₄ alkyl or phenyl. Izv. Sib. Otd. Akad. Nauk SSSR, Ser. Khim. Nauk 1975, (5), 100–6.

SUMMARY OF THE INVENTION

The present invention is drawn to a process for preparing cyano-containing difunctional derivatives of pentafluorobenzonitrile, compounds produced therefrom and derivatives of such compounds. The compounds of this invention are extremely useful as intermediates in the synthesis of either cyclopropane carboxylates or high temperature stable polymers.

DETAILED DESCRIPTION OF THE INVENTION

The compounds of this invention may be represented by the formula:

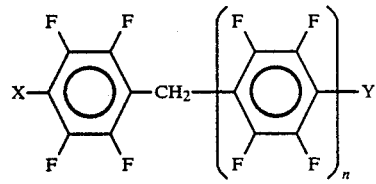

wherein X and Y for any given compound are identical substituent groups and are selected from the class consisting of

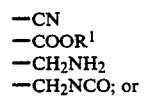
—CN
—COOR¹
—CH₂NH₂
—CH₂NCO; or

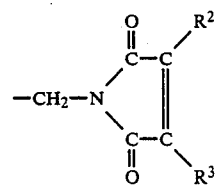

wherein for any given compound:
(i) R¹ may be either hydrogen or an alkyl group;
(ii) R² and R³, independent of one another, are either hydrogen, halogen or alkyl; and
(iii) n is either 0 or 1.

The alkyl group for R¹ preferably contains 1 to 6 carbon atoms and for R² and R³ preferably contains 1 to 4 carbon atoms. Further, the halogen atom for R² and R³ is preferably a chlorine, bromine or fluorine atom. Thus, while R¹, R² and R³ are independent of one another, each of R¹, R² and R³ are represented by one substituent for any given compound. Likewise, X and Y are both represented by only one of the aforementioned substituents for any given compound.

While useful as intermediates in the production of insecticides and high temperature stable polymers, it was further found that these compounds may increase cohesive strength and tackiness in synthetic rubber compositions.

The compounds wherein X and Y are both —CN are the precursors for the other compounds of this invention. These compounds may be produced in good yields by a Grignard synthesis. In particular, these compounds are produced by reacting pentafluorobenzonitrile (PFBN) and a Grignard reagent of the formula CH₃MgHal, wherein Hal is either chlorine or bromine, in a reaction medium. The principal products obtained are of the formula:

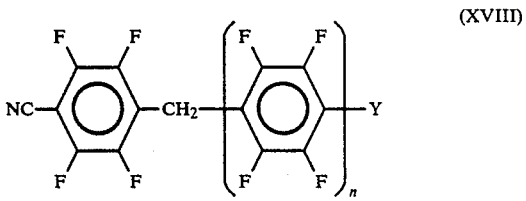

The selection of the solvent is critical, however, upon the yield obtained and the resulting product. The solvents demonstrating a dramatic effect on the product distribution are:

1. 1,3-Dioxolane. It was discovered that use of the solvent 1,3-dioxolane renders the substitution of the —CH₂CN group for the fluorine group of PFBN. The resulting compound, 4-cyano-2,3,5,6-tetrafluorobenzyl cyanide, represented by formula (XVIII) wherein Y is —CN and n is 0, is especially useful as an intermediate in the production of specialty polymers. Further, by employing 1,3-dioxolane as solvent, only small amounts of 3-methyl-4-cyano-2,5,6-trifluorobenzyl cyanide, 2,3,5,6-tetrafluoro-p-toluonitrile and 4-acetyl-1,2,3,5,6-pentafluorobenzene by-products are obtained.

2. Tetrahydrofuran. When the reaction is conducted in the presence of tetrahydrofuran (THF), the principal product obtained is 4,4′-methylene bis(tetrafluorobenzonitrile) (bis TFBN); as represented by formula (XVIII) above wherein Y is —CN and n is 1. This compound is likewise suitable as an intermediate in the production of polyesters and polyamides.

3. Dimethoxyethane and Diglyme. It was further discovered that when the reaction is conducted in the presence of either dimethoxyethane (DME) or diglyme, the principal product obtained is 2,3,5,6-tetrafluoro-p-toluonitrile (TFTN). This product may further be represented by formula (XVIII) wherein n is 0 and Y is H. This compound may be employed as an intermediate in the synthesis of pesticidal compounds as disclosed in U.K. Patent Application No. 2,135,306A. Especially desirous results are obtained when the solvent employed is DME. It is most preferable to use redistilled DME or DME treated with molecular sieves (Aldrich 13×, 8 mesh) in order to avoid any side reactions involving peroxide impurities.

Thus, the reaction of PFBN and the Grignard reagent is solvent specific; TFTN being the major product when the solvent is either DME or diglyme; bis TFBN being the major product when the solvent is THF; and 4-cyano-2,3,5,6-tetrafluorobenzyl cyanide being the major product when the solvent is 1,3-dioxolane.

The PFBN and Grignard reagent are generally reacted between 0.25 and 4 hours, preferably between 1 and 2 hours, between −20° C. and 35° C. The preferred temperature range is 10°–25° C. Generally, the desired reaction will proceed more slowly at the lower end of the temperature range than at the higher end. For example, when tetrahydrofuran is employed as solvent, the reaction may be completed in 10 minutes at 10° C. with a moderate excess of Grignard reactant being employed versus in several hours at −20° C. with a lower excess of Grignard being employed. The reaction is terminated by the addition of either 0.5N to 6N, preferably 4N, acid solution, preferably HCl or NH₄Cl or water.

The molar ratio of Grignard reagent to PFBN is between 1.0 and 3.0, most preferably between 1.2 and 1.6. Generally at the lower end of this scale the reaction may be incomplete whereas the formation of bis TFBN and higher condensation products are favored at the higher end.

The PFBN is generally dissolved in the solvent media prior to admixing the Grignard reagent. The amount of PFBN to solvent is from 1:3 to 1:30 (weight/volume), preferably between 1:6 to 1:15, most preferably 1:10. Further, the Grignard reagent is preferably dissolved in an organic solvent, such as tetrahydrofuran (THF) and diethyl ether, most preferably tetrahydrofuran, prior to admixing it with the PFBN solution. The concentration of Grignard reagent in the organic solvent is preferably between 2.0 and 3.5 molar.

In the Grignard reagent, Hal is either —Cl or —Br. Since the use of CH₃MgBr leads to greater by-product formation, particularly, 3-methyl-4-cyano-2,5,6-trifluorobenzyl cyanide, the Grignard reagent preferably contains a chlorine atom for the X substituent, when the solvent is 1,3-dioxolane.

The reactant pentafluorobenzonitrile (PFBN) may be commercially obtained. Alternatively, it may be obtained by fluorinating the commercial product pentachlorobenzonitrile with potassium fluoride in a polar aprotic solvent.

The compounds of formula (XVII) wherein X and Y are —CN are especially useful as intermediates in the production of high stable polyesters and polyamides since the cyano groups can easily be hydrolyzed or hydrogenated, respectively. For example, the compound can be catalytically hydrogenated according to the reaction

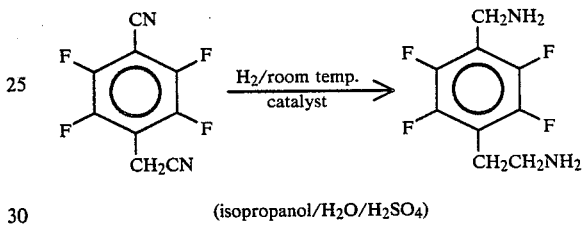

(isopropanol/H₂O/H₂SO₄)

Further, the compound could be hydrolyzed by dilute acid according to the reaction

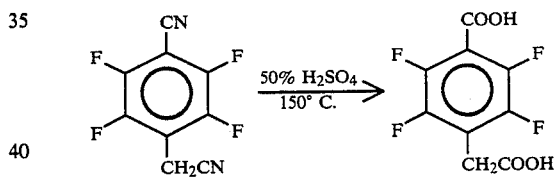

The corresponding diisocyanate and N,N′-bismaleimide can further be prepared from the reduced product and subsequently employed in the production of polyurethanes and thermoplastic polymeric products, respectively. For example, such compounds can be prepared by reacting the diamine with an acid anhydride, such as maleic anhydride, and then reacting the resulting maleamic acid with acetic anhydride and an alkali acetate to yield the desired N,N′-bis-maleimide. This reaction may be summarized as:

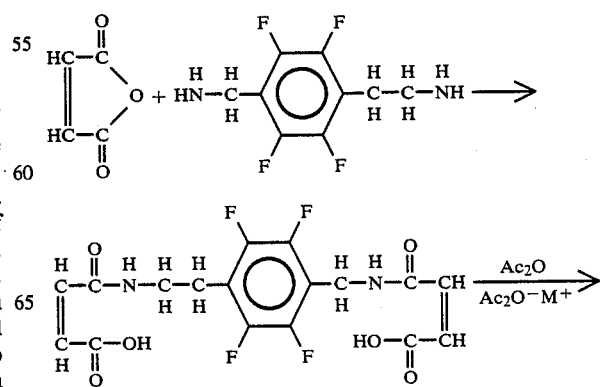

-continued

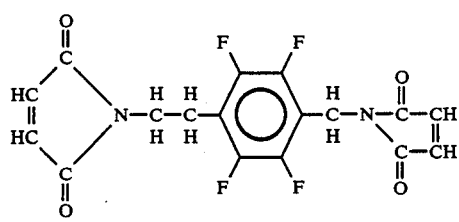

The examples which follow are presented to illustrate the invention and the advantages thereof. They are not, however, intended to limit the scope of the invention.

EXAMPLE 1

A 2.8 molar solution of methyl magnesium chloride in 115 ml. of tetrahydrofuran (THF) was added dropwise to a stirred solution of 30.9 g. of pentafluorobenzonitrile in 300 ml. of tetrahydrofuran under nitrogen between −15° to −20° C. The addition was complete in 28 minutes. The reaction product was then stirred for 1 hour at −15° C. To this solution was slowly added, 150 ml. THF/H$_2$O (1:1 v/v), followed by 150 ml. of 4N HCl solution. The product was stirred at room temperature until all solids were dissolved. The uppermost product layer was separated and evaporated to a small volume, then dissolved in 175 ml. of methylene chloride. This methylene chloride solution was then washed with 25 ml. of water four times followed by 25 ml. solution of 5% sodium bicarbonate and 25 ml. of water. The methylene chloride solution was then vacuum stripped at 45° C./25 mm to render 27.2 grams of product. Analysis by gas liquid chromatography indicated that 40% of this product waas bis TFBN, and 20% TFTN. This product was left to crystallize at room temperature for approximately 24 hours and, after filtration, and removing the filtrate a light yellow solid identified as 4,4'-methylene bis(2,3,5,6-tetrafluorobenzonitrile) (bis TFBN), and having a melting point between 112°–115° C. after washing with methanol, was obtained. Recrystallization from 5 parts of methanol gave pure 4,4'-methylene bis(2,3,5, 6-tetrafluorobenzonitrile) (bis TFBN), with a melting point between 114°–116° C. The compound had the following chemical analysis: C, 49.78%; H, 0.62%; F, 39.42%; and N, 7.86%. Calc: C, 49.75%, H, 0.56%; F, 41.98%; and N, 7.73%. 4,4'-Methylene bis(2,3,5,6-tetrafluorobenzonitrile) (bis TFBN) was identified by NMR and GC/MS. The filtrate was then fractionally distilled in a Vigreux column under high vacuum at 170° C./8mm. 5.8 grams of a colorless liquid distilling at 72°–75° C./8 mm Hg. was obtained. This compound was identified by NMR and GC/MS as 2,3,5,6-tetrafluoro-p-toluonitrile (TFTN). The distillation residue, not distillable below a pot temperature of 170° C./8 mm was crystallized on standing at room temperature. This product weighing 14.0 grams was identified by NMR and GC/MS as being predominantly 4,4'-methylene bis-(2,3,5,6-tetrafluorobenzonitrile) (bis TFBN) and may be further purified by recrystallization from methanol at 0° C.

EXAMPLE 2

Pentafluorobenzonitrile (17.8 g.) was dissolved in 178 ml. of 1,3-dioxolane. The resulting solution was cooled to 20° C. The solution was stirred under nitrogen while adding 48 ml. of methyl magnesium chloride solution in tetrahydrofuran (2.8 M) dropwise during a period of 35 minutes while the temperature was maintained at 20° C. with occasional cooling. Stirring was then continued at 20° C. for one hour. To the resulting solution was gradually added 38.4 ml. of 4N HCl at 15°–22° C. and 154 ml. of methylene chloride. The mixture was then stirred and allowed to separate. The lower acidic phase was discarded and the organic layer was washed five times with a mixture of 56 ml. of water and 20 ml. of brine (a 10% by wt. sodium chloride solution obtained by mixing 100 g of sodium chloride in 1 liter of water) until the pH was 3.5. 16.1 g of crude product was then isolatled by stripping in vacuum. The crude product was then purified by distilling at a boiling point between 122°–128° C./1 mm. The yield was about 65%. The product was further purified by treating it with a small amount of methanol, approximately 4 g. of product to 1 ml. of methanol, and crystallizing the resulting product at 0° C. The purified product was then isolated by filtration. The melting point of the product was between 48°–52° C. Analysis by gas liquid chromatography indicated the product was 85–90% pure. The compound was identified by mass spectrometry and NMR to be 4-cyano-2,3,5,6-tetrafluorobenzyl cyanide.

Analysis: C, 49.79%; H, 1.09%; N, 12.12%.
Calc: C, 50.48%; H, 0.94%; N, 13.08%.

EXAMPLE 3

PFBN (32.6 g) was dissolved in 325 ml of DME. A 2.8 molar solution of methyl magnesium chloride in THF (85 ml) was then added to the stirred PFBN solution dropwise under N$_2$ at 0°–5° C. in 1 hr. The reaction was continued for 1½ hours at 0°–5° C. and was then terminated by adding 4N HCl (74 ml) slowly at 5° C. The product consisted of two layers. After addition of 275 ml methylene chloride, the aqueous layer was separated and discarded. The product solution was washed once with 150 ml H$_2$O and three times with brine. The solvents were distilled off at 40°–60° C. under slight to moderate vacuum and TFTN was then recovered from the solvent-free product by distillation at 65°–70° C./6 mm and identified by NMR and GC/MS analysis. The yield of high purity TFTN was 11.3 g.

EXAMPLES 4–5

The experimental procedure of Examples 2 and 3 was repeated under the conditions indicated below. GC analysis demonstrated the product distribution as indicated.

| Example | Molar Ratio of CH$_3$MgCl PFBN | Reaction Temperature | Reaction Time | Solvent |
|---|---|---|---|---|
| 4 | 1.125 | −15° to −20° C. | 1 hr. | THF |
| 5 | 1.185 | 25° C. | 0.5 hr. | THF |

| | GC Analysis (Product Ratios) | |
|---|---|---|
| PFBN | TFTN | bis TFBN |
| 25 | 22 | 36 |
| 1 | 13.8 | 26.9 |

EXAMPLE 6

Pentafluorobenzonitrile (1 g.) was dissolved in 10 ml. of dimethoxyethane. The solution was stirred at room temperature. 2.5 ml of a 2.8 molar solution of methyl magnesium chloride in tetrahydrofuran was added slowly to the solution while the temperature was maintained at 25° C. through occasional cooling. After a reaction period of approximately 30 minutes, 2 ml of 4N HCl and 8 ml. of methylene chloride was added. The methylene chloride solution was separated and washed four times with 3 ml. of water or 3 ml. of an aqueous brine solution. Diphenyl ether (0.25 g.) was added to the reaction in order to facilitate GC analysis. The GC analysis indicated that a product ratio of 29:20 of 2,3,5,6-tetrafluoro-p-toluonitrile (TFTN) and 4,4'-methylene bis(2,3,5,6-tetrafluorobenzonitrile) (bis TFBN) was obtained.

EXAMPLES 7–12

The experimental procedure of Example 6 was repeated employing the following parameters:

| Example | Molar Ratio of $CH_3MgCl$/ PFBN | Amount of 2.8 Molar $CH_3MgCl$ added (ml) | Reaction Temperature | Reaction Time |
|---|---|---|---|---|
| 7 | 1.10 | 2.1 | 25° C. | 0.5 hr. |
| 8 | 1.20 | 2.2 | 25° C. | 0.5 hr. |
| 9 | 1.26 | 2.3 | 25° C. | 0.5 hr. |
| 10 | 1.29 | 2.4 | 0° C. | 1.0 hr. |
| 11 | 1.40 | 2.6 | 0° C. | 0.5 hr. |
| 12 | 1.51 | 2.8 | −10° C. | 2.0 hr. |

GLC Analysis rendered the following product distribution (ratio).

| | PFBN | TFTN | bis TFBN |
|---|---|---|---|
| 7 | 40 | 25 | 11 |
| 8 | 11 | 26 | 8 |
| 9 | 15 | 24 | 6.5 |
| 10 | 11.2 | 30 | 18 |
| 11 | 5.2 | 32 | 21 |
| 12 | 14 | 28 | 18 |

The yield of 2,3,5,6-tetrafluoro-p-toluonitrile (TFTN) in Example 10 measured by GLC against diphenylether, the internal standard, was approximately 44% with 17% pentafluorobenzonitrile being unreacted. The yield of 4,4'-methylene bis(2,3,5,6-tetrafluorobenzonitrile (bis TFBN) was 22%. The examples illustrate the reversal of 2,3,5,6-tetrafluoro-p-toluonitrile (TFTN): 4,4'-methylene bis(2,3,5,6-tetrafluorobenzonitrile (bis TFBN) ratio in the products when dimethoxyethane is used as solvent instead of tetrahydrofuran.

EXAMPLE 13

To a one liter round bottom flask is added 100 g of the compound of Example 2 and 300 ml of an 18 N sulfuric acid solution. The solution is heated for 4 hours at 130°–150° C. The resulting acid is isolated by adding the resulting crude product solution to 1 liter ice water and filtration. The product is then washed with water and dried.

EXAMPLE 14

To a one liter round bottom flask is added 100 g of the compound of Example 1 and 300 ml of an 18 N sulfuric acid solution. The solution is heated for 6 hours at 150°–170° C. The resulting acid is isolated by adding to 1 liter ice water and filtration. The product is washed with water and dried.

EXAMPLE 15

Into a 300 ml autoclave is added 10 g of the compound of Example 1, bis TFBN, 22 ml of isopropanol, 26 ml of water, 7.2 g of concentrated sulfuric acid and 1.5 g of 5% Pd/C. After flushing with nitrogen, 880 psi of hydrogen pressure is applied and stirring at room temperature is continued for 5.5 hours. The reaction mixture is filtered and carefully washed with aqueous isopropanol. Isopropanol is then removed by distillation and an aqueous sodium hydroxide solution is slowly added to the residue until the pH is basiC. The product is then dissolved in ether and dried with $Na_2SO_4$. After evaporation of the solvent, the product obtained is a white solid.

EXAMPLE 16

7 Parts of chlorobenzene are stirred and cooled to −7° C. in a reaction vessel. 2 Parts of phosgene is then introduced into the reaction vessel. 1.5 Parts of the reaction product of Example 15, 4,4'-methylene bis(2,3,5,6-tetrafluoro)benzylamine, are gradually added to the solution and stirring is then continued at a temperature which ranges between 25 and 40° C. while additional phosgene is slowly introduced. After the mild exothermic reaction has subsided, the solution is stirred for 2 hours at a temperature between 60 and 80° C. Negligible residual HCl evolution occurs at the end of the reaction. The product solution is then sparged with nitrogen, filtered and stripped in vacuum until a viscous syrup is obtained. The diisocyanate product may be purified by extraction with hexane.

EXAMPLE 17

3.3 Mol of maleic anhydride is dissolved in 350 ml of acetone, and the solution obtained is introduced into a 2-liter reactor provided with a stirrer and a thermometer. The reactor is further placed in a cooling bath consisting of a mixture of water and ice. 1.5 Mol of the compound of Example 15 in solution in 800 ml of solvent consisting of a mixture of dimethyl formamide and chloroform in equal volumes is slowly introduced into the reactor with vigorous stirring. The rate of flow is so adjusted that the temperature of the reaction mass remains below 20° C. The bismaleamic acid compound precipitates as it is formed and is recovered by filtration at the end of the reaction. The product is washed with acetone and dried. 0.5 Mol of the bis-maleamic acid is then introduced into a reactor which is provided with a thermometer, a central stirring system, and can be heated by a water bath. The following ingredients are introduced into the reactor:

1.5 mol of acetic anhydride,
300 ml of dimethyl formamide,
10 g of sodium acetate.

The temperature is gently raised to 60° C., and the reaction mass is maintained at this temperature for 1 hour. After cooling to 15° C., the excess of anhydride is destroyed by adding a little water, and the bisimide crystallizes out. After filtration, the product is washed with water and dried.

Preparation A: Synthesis of a Polyester with a Final Acid Value of Appoximately 25 and a Low Softening Point.

0.2 Mol of ethylene glycol and 0.2 mol of neopentyl glycol are introduced into a 250 ml round bottom flask, fitted for stirring, heating, distillation, addition of reactants and maintenance of an inert gas atmosphere. After sweeping the flask with nitrogen, slow stirring and heating are begun and 0.02 grams of a technical grade of hydroquinone (polymerization inhibitor) is added.

Thereafter slow addition of 50 grams of the acid of Preparation A is begun and distillation starts at 150°–170° C. After reaching cooking temperature (210° C.), 20 g maleic anhydride is added and the mixture is heated under nitrogen with stirring for 8 hours. Vacuum is applied to the system for 30 minutes before the end of the cook. The resin is then poured into a flat aluminum tray to cool, harden and subsequently broken up and ground. The final acid value of the resinous product is approximately 25 and has a low softening point.

Preparation B: Synthesis of a Polyester with a Moderately High Softening Point.

0.2 Mol of ethylene glycol and 0.2 mol of neopentyl glycol are introduced into a 250 ml round bottom flask, fitted for stirring, heating, distillation, addition of reactants and maintenance of an inert gas atmosphere. After sweeping the flask with nitrogen, slow stirring and heating are begun and 0.02 grams of a technical grade of hydroquinone (polymerization inhibitor) is added. Thereafter slow addition of 80 grams of the acid of Preparation B is begun and distillation starts at 150°–170° C. After reaching cooking temperature (210° C.), 20 g maleic anhydride is added and the mixture is heated under nitrogen with stirring for 8 hours. Vacuum is applied to the system for 30 minutes before the end of the cook. The resin is then poured into a flat aluminum tray to cool, harden and subsequently broken up and ground. The final acid value of the resinous product is approximately 25 and has a moderately high softening point.

Preparation C: Synthesis of a Synthetic Rubber Composition Having Increased Cohesive Strength and Tackiness.

100 parts by weight (pbw) of polyisoprene, 1.5 pbw of low molecular weight butadiene rubber containing 5% of nitrosodiphenylamine groups, 0.1 pbw of the acid of Preparation A, 0.5 pbw of sulphur, 0.4 pbw of dibenzylthiazolyl disulphide, 1.0 pbw of diphenyl guanidine, 1.0 pbw of stearic acid, 2.0 pbw of zinc oxide and 20 pbw of technical carbon was milled and then vulcanized for 20 minutes at 406 K. The cohesion and tackiness of the resulting composition was equal to that of natural rubber.

What is claimed is:

1. The compound of the formula

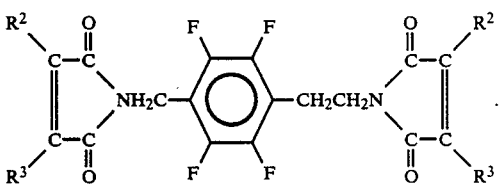

2. The compound of the formula

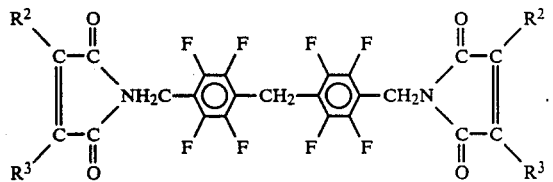

* * * * *